US 6,614,015 B1

(12) United States Patent
Ba et al.

(10) Patent No.: US 6,614,015 B1
(45) Date of Patent: Sep. 2, 2003

(54) DETECTOR OF STAINS ON A TRANSPARENT PLATE SURFACE

(75) Inventors: LoanMy Le Ba, Billancourt (FR); Jacques Sabater, Gif sur Yvette (FR)

(73) Assignee: Valeo Systems d' Essuyage (FR)

( * ) Notice: Subject to any disclaimer, the term of this patent is extended or adjusted under 35 U.S.C. 154(b) by 0 days.

(21) Appl. No.: 09/869,620

(22) PCT Filed: Dec. 15, 1999

(86) PCT No.: PCT/FR99/03171

§ 371 (c)(1),
(2), (4) Date: Sep. 10, 2001

(87) PCT Pub. No.: WO00/40443

PCT Pub. Date: Jul. 13, 2000

(30) Foreign Application Priority Data

Dec. 30, 1998 (FR) .......................................... 98 16615

(51) Int. Cl.[7] ................................................ G02B 6/42
(52) U.S. Cl. ............................ 250/227.24; 250/227.25; 250/216; 340/602; 318/483
(58) Field of Search .......................... 250/216, 227.24, 250/227.25, 339.1, 339.11, 341.8, 513, 514; 15/DIG. 15; 73/29.01; 340/602; 318/483; 356/135, 136

(56) References Cited

U.S. PATENT DOCUMENTS

| 4,652,745 A | 3/1987 | Zanardelli | 250/227 |
|---|---|---|---|
| 4,701,613 A | 10/1987 | Watanabe et al. | 250/227 |
| 4,871,917 A | 10/1989 | O'Farrell et al. | 250/341 |
| 5,323,637 A | 6/1994 | Bendicks et al. | 73/29 |
| 5,773,825 A | * 6/1998 | Doyle | 250/339.11 |
| 6,018,165 A | * 1/2000 | Kerkmann et al. | 250/574 |
| 6,307,198 B1 | * 10/2001 | Asakura et al. | 250/227.25 |
| 6,507,015 B1 | * 1/2003 | Maeno et al. | 340/602 |

FOREIGN PATENT DOCUMENTS

| DE | 38 06 881 | 9/1989 |
|---|---|---|
| DE | 40 33 975 | 5/1991 |
| DE | 40 19 066 | 12/1991 |
| DE | 43 43 474 | 7/1994 |
| DE | 43 94 343 | 8/1994 |
| DE | 43 29 608 | 1/1995 |
| DE | 43 29 983 | 3/1995 |
| DE | 44 10 217 | 9/1995 |

* cited by examiner

Primary Examiner—Stephone B. Allen
(74) Attorney, Agent, or Firm—J. Gordon Lewis

(57) ABSTRACT

A detector of stains on a transparent plate surface is arranged on an internal surface of the plate and includes an emitter for emitting a modulated light signal towards the inside of the plate and a receiver for receiving the signal after it has been reflected on an external surface of the plate. An optical unit made with a material having an index substantially higher than the plate, is arranged on the internal surface of the plate. The optical unit is made up of at least three faces returning the light signal and an interface with the internal surface of the plate through an optical coupler. A deflector deflects the signal from the emitter toward the plate and from the optical unit towards the receiver. At least two reflections on the external surface of the plate are produced through the optical coupler without reflection on the internal surface of the plate.

22 Claims, 2 Drawing Sheets

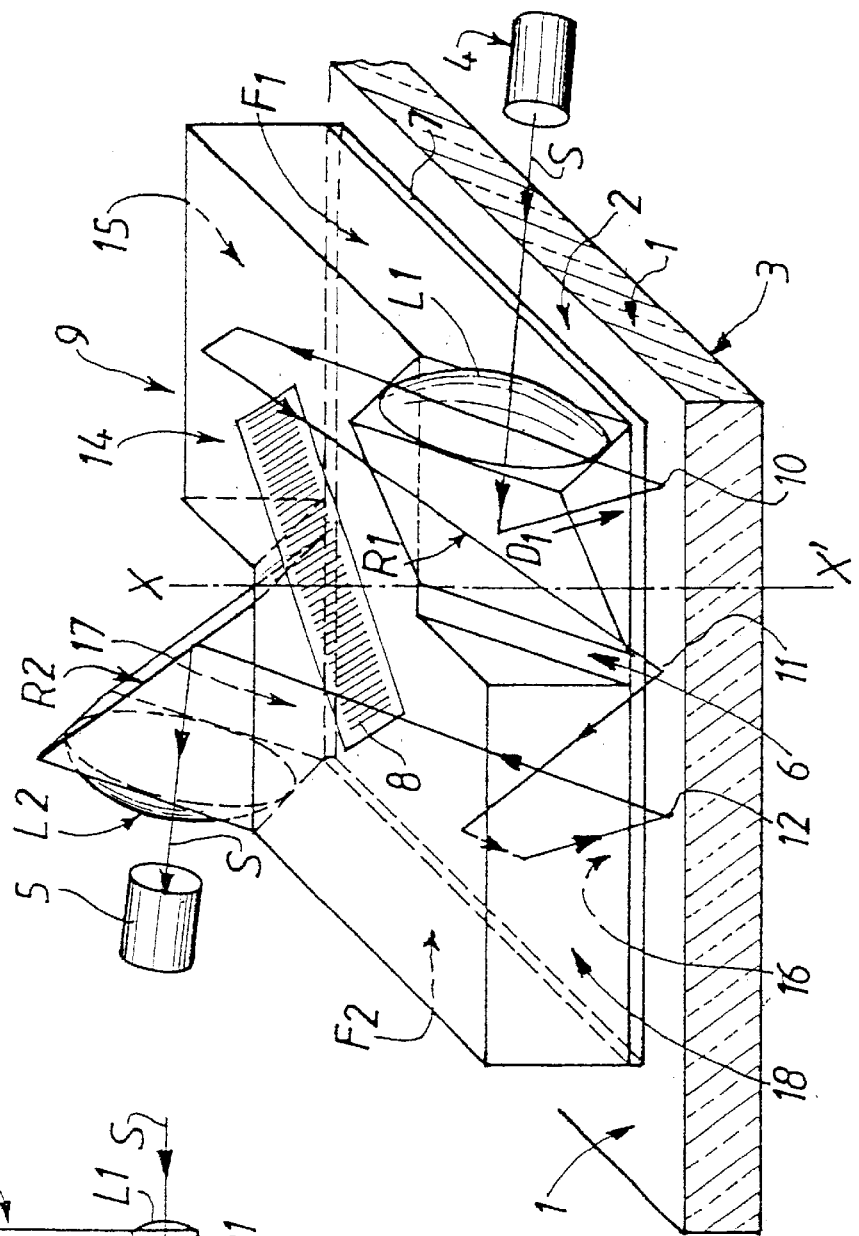
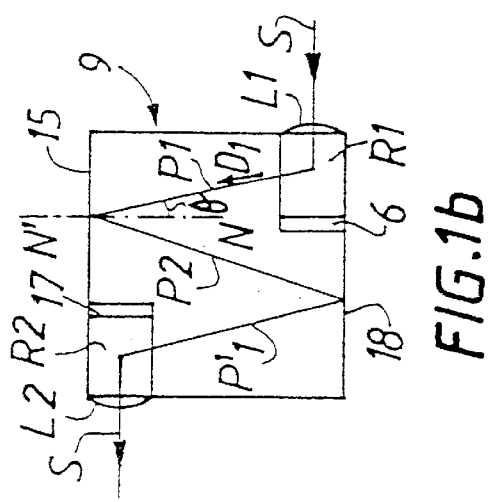
FIG.1a
FIG.1b

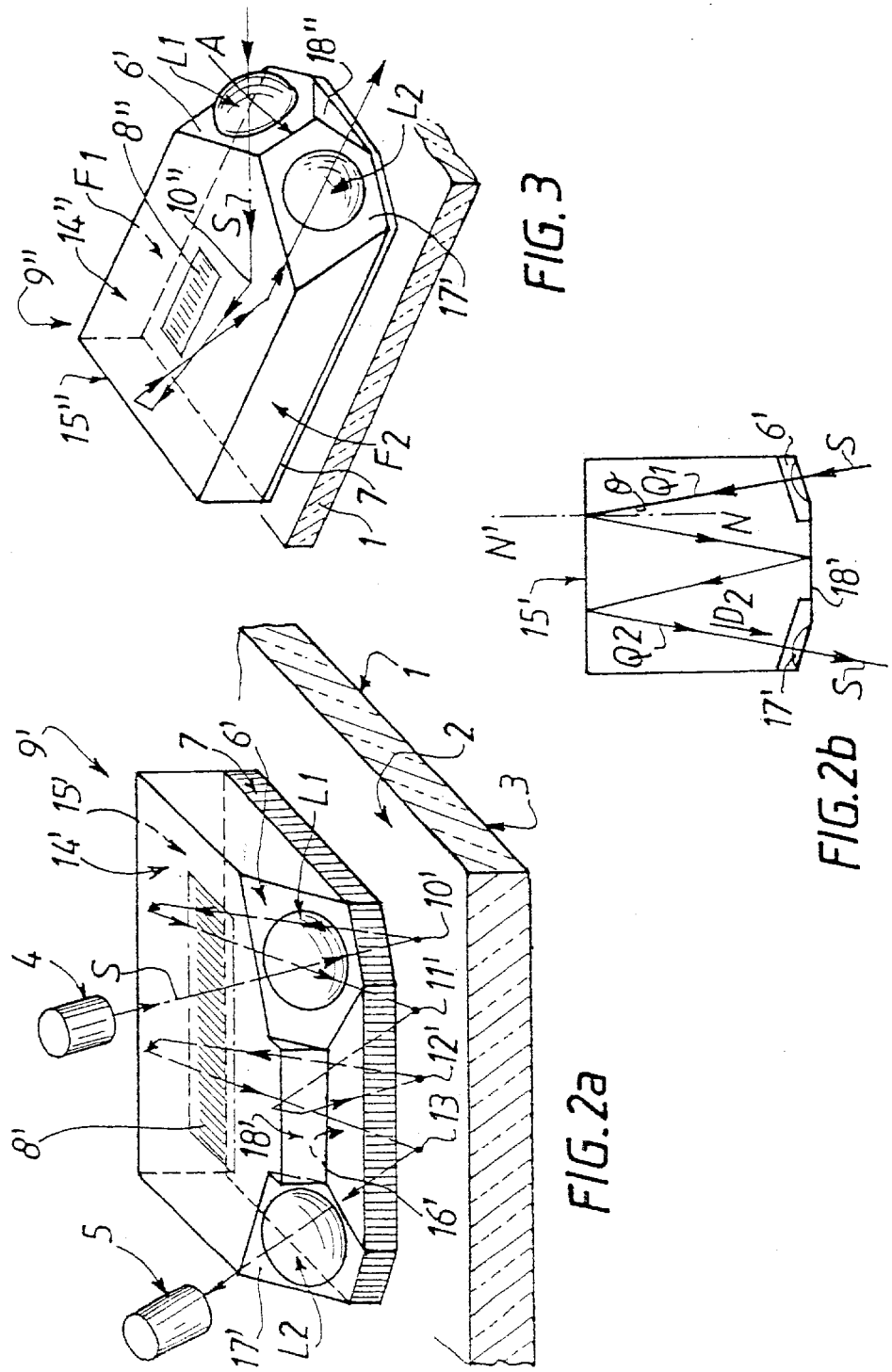

DETECTOR OF STAINS ON A TRANSPARENT PLATE SURFACE

BACKGROUND

The invention concerns a detector of stains on a plate surface transparent to visible rays, in particular, a motor vehicle window.

The invention concerns, more specifically, a detector of stains, for example liquid, on the surface of a transparent plate that has two opposite sides notably parallel, and an internal face and an external face defining an interior volume.

In this type of detector, an emitter is arranged on the internal face of the plate and emits a modulated light signal in the direction of the interior of the plate such that the signal penetrates the plate. While the signal hits one of the faces of the plate, the signal is reflected towards the interior of the plate if this face is in contact with the air or altered, that is to say, refracted, focalized, absorbed, diffused, etc., in the case where the face is in contact with the stains to detect. Stains are defined here to be all deposits having an aqueous component, such as rain, snow, frost, mud, etc.

This type of device also comprises a receptor arranged in a target zone of a face of the plate such that the signal that moves around in the plate, when it hits the target zone, is reflected and is received by the receptor.

Such detection devices allow, for example, controlling the activation of motor vehicle wipers when drops of water appear on the windshield.

As a function of the material of the windshield and the length of the electromagnetic signal wave, the angle of incidence of the modulated light signal is chosen in such a manner that the ray is reflected in the direction of the internal face of the windshield if the external face is in contact with the air at the level of the impact zone of the signal and in such a manner that the ray is at least partially refracted towards the exterior if the water or stain covers the impact zone of the external face.

If the ray is reflected, it will be guided to follow its route to the interior of the windshield, in the thickness of the glass, in order to be reflected several times by the internal and external faces of the windshield. In a place of the internal face that is on the trajectory of the signal, one has places for optical coupling means, the refraction index of which is such that the signal is refracted across the internal face of the windshield in order to be transmitted to an adapted receptor.

In this way, if the receptor captures a signal higher than a determined threshold, no stain at the level of the impact zones of the signal against the external face of the windshield is detected. On the other hand, if the receptor no longer receives a signal (for example, due to absorption, diffusion, or refraction), where if it receives a signal at a level notably higher (for example from focalizing), the presence of stains, for example, drops of water, are present on the exterior face of the windshield.

One has however noted that in such a unit, the signal received by the receptor was slightly higher. In order to augment the level of detection, in particular the detection of fine, small drops in small numbers, the number of reflections of the signal on the external face of the plate was multiplied by detecting the modulated light after having been reflected several times and alternatively on the external face and on the internal face of the plate.

This method's inconveniences are that it is particularly sensitive to the deposits of condensation on the internal face of the plate, imposing a relatively precise positioning of the emitter and receptor parts, and that it is particularly sensitive to the variations and imperfections of the thickness of the plate.

SUMMARY

The invention aims to eliminate these inconveniences by proposing a detector that is at the same time compact and likely to supply an adapted number of reflections on the face to survey, by exploiting the principle of total reflection.

More precisely, the invention concerns a detector of stains on the surface of a transparent plate that has two notably parallel, opposite sides, an internal face and an external face. Such a detector, arranged on the internal face of the plate, comprises means emitting a modulated light signal in the direction of the interior of the plate, and means receiving this signal after having been reflected on the external face of the plate, and an optical unit made with material having an index substantially higher than one and transparent to the radiance of the modulated light signal. The optical unit is placed on the internal face of the plate and is made up of at least two faces deflecting the light signal, in order to form a trajectory between the emission means and the receiving means, and from the bottom interface with the internal face of the plate across the means of optical coupling. Also planned: deviation means of the signal from the emission means, so that the signal reflects a first time on the external face of the plate according to a direction included in an initial incidence plane, and deviation means of the signal towards the receiving means so that the faces of deflection thus orient the signal successively towards the external face in at least one incidence plane notably not parallel in the initial incidence plane so that the trajectory of the light signal between the emission means and receiving means produce at least two reflections on the external face of the plate across the optical coupling means without reflection on the internal face of this plate.

Thus, the trajectory of the signal, between the emission and reflection means, is notably confined in the optical unit and in the volume of the plate situated opposite from the unit.

According to the specific modes of production of the invention:

- the optical unit is, on the whole, outlined according to a parallelepiped rectangle having mainly a front face, an upper face, a rear face, two lateral faces, and a bottom face that interfaces with the plate;
- the deflection faces are made up of a rear face, the upper face and the front face, or by the front face and the rear face, these two faces being inclined in order to make a deflection signal towards the plate;
- the light signal penetrates the optical unit after deviation via an input face situated in the front face of the optical unit, and leaves from the front deviation optical unit on the receiving means via an output face situated in the front face while the number of reflection on the external face of the plate is even, and in the rear face when the number of reflections is odd;
- the input and output faces of the unit form lenses, which can be coupled to an optical deflection in order to make up the deviation means;
- at least one of the lenses is a convex lens comprising at least a non-spherical or spherical surface, where there is a Fresnel lens, the lenses can make up an integral part of the optical unit;

the optical coupling means are formed via a flexible layer of transparent material in the light signal, for example, silicon, the layer being compressed between the bottom face of the optical unit and the internal plate face;

an interferential filter is planned between the output face and the receiving means attached on the spectral band of the signal in order to eliminate light interference;

the optical unit and the optical coupling means are mass-colored to eliminate light interference;

a heating element is placed near or against one of the faces of the optical unit in order to eliminate condensation; thanks to the compactness of the detector the condensation is eliminated in an efficient and rapid manner;

the emitting means can be made up of an electro luminescent diode or by a photodiode, and the receiving means by a silicon photo detector cell, the emitting diode and the receiving cell can be placed near each other;

the emitting and receiving means are connected to a treatment unit formed on a printed circuit board in order to produce a modulation in amplitude for the signal of the emitting diode and a synchronous detection of the signal received by the photo detector cell;

the deflection faces are subjected to a treatment reflecting the light signal, for example, an aluminizing, where they are recovered with a layer of material reflecting the light signal;

the faces of the optical unit, other than the deflection faces and the interface, are covered with a material that absorbs the light signal.

BRIEF DESCRIPTION OF THE DRAWINGS

Other characteristics and advantages of the invention will become clearer in the reading of the description of a method of production that follows, referring to the attached drawings that represent, respectively:

FIGS. 1a and 1b are schematic views in perspective and from the top of an example of a detector conforming to the specifications of the invention;

FIGS. 2a and 2b are schematic views in perspective of another production example of the detector according to the invention; and FIG. 3 is a schematic view in perspective of a variance of the optical unit of the detector according to FIG. 2.

DETAILED DESCRIPTION

Illustrated in FIG. 1 a is a plate 1 made of a transparent material that comprises two opposite faces internal 2 and external 3 notably in parallel. In the illustrated example, the plate 1 is notably flat, but the invention could be used in cases of a plate presenting curved shapes, as is the case, for example, for motor vehicle windows, and specifically the windshield.

According to the invention, the plate 1 carries a stain detector made up of an optical unit 9, placed to the side of the internal face 2 of the plate 1, and which is designed to detect the presence of stains, for example, drops of water, on the external face 3 on the plate. The optical unit according to this non-limiting example possesses a central symmetrical axis X'X.

The detector also comprises an emitter 4 and a receiver 5. The emitter 4 is an electro luminescent diode that emits a light signal S in modulated light, close to infrared in the production example, but which can be in visible light in other examples. The receiver 5 is a silicon cell.

The light signal is emitted in the direction of the optical unit 9 that is created in the shape of a body in a plastic transparent material, for example, PMMA (polymethyl methacrylate plastic) with an average index equal to 1.48 in a shape of, on the whole, a parallelepiped rectangle, and with dimensions roughly equal to $25 \times 25 \times 5$ mm$^3$. The unit can be created in another plastic material (poly carbonate, polyethylene, etc.) or in glass.

This unit has faces outlined by dedicated planes, that is to say:

a front face 18 and a rear face 15, in which are outlined, respectively, inclined input 6 and output 17 faces of the light signal S; these input and output faces 6, 17 being outlined in order to form, in relation to the normal axis X'X of the plate 1, an angle equal to 45°;

an upper face 14 and a bottom face 16 interfacing with the plate 1 via a silicon layer 7; and two lateral faces F1 and F2, that complete the outline of the unit.

Between the bottom face 16 of the unit and the internal face 2 of the plate 1, the silicon layer 7, outlined according to the perimeter of the bottom face 16, assures an optical continuity of the route of the light signal by creating a total refraction to the interface 16-2 or 2-16—that is to say, respectively: bottom face 16 on internal face 2, or internal face 2 on bottom face 16—whatever the direction of the route of the signal S. The silicon layer 7 forms an adequate optical coupling means from the fact that its refraction index is close to that of the unit 9 and of the plate 1: the possibilities of reflection of the signal are thus considerably reduced while the signal passes through the interface 16-2 or 2-16.

The reflection of the signal on the deflection faces shows the total reflection in the measure where the angle of incidence on these value of penetration in the unit after deviation, stays higher than the refraction angle limit.

Put side by side respectively on the input and output faces, 6 and 17, the optical deflections R1 and R2 are coupled to deviation lenses L1 and L2 allowing the orientation of the signal S in the optical unit to leave the emitting diode 4 and towards the receptacle cell 5 upon leaving from the unit. The lenses L1 or L2 form non-spherical revolution surfaces. The lenses can be stuck to the input and output faces of the unit or on the optical deflections, or make up an integral part of the optical unit via casting the unit ensemble, deflections and lenses.

The signal S follows a optical trajectory oriented in order to create an odd number of reflections on the external face of the plate 1, three reflections 10, 11, 12 in the example, with four deflections in the optical unit 9 between the emitting diode 4 and photoreceptor cell 5, being on the rear 15, upper 14, and front 18 faces.

After deviation via optical means L1 and R1, the signal S orients itself according to the direction D1 forming an angle roughly equal to 45° with the normal X'X, this direction being included in an initial incidence plane P1 perpendicular to the plate 1.

The trace of the plane P1 is visible on the top view illustrated in FIG. 1b. In relation to a normal N'N to the input and output faces, 6 and 17, the plane P1 forms an angle θ adapted, roughly equal to 13° in order to produce the wanted number of reflections on the external face of the plate and of deflections in the optical unit, respectively three and four in the example between the emitting and receiving means.

The signal S thus follows the following optical trajectory:

after the crossing of the interface 16-2 and a first reflection on the external face 3 of the plate 1, in an elementary referenced zone 10, followed by a crossing of the interface 2-16, it is returned by the rear 15 and upper 14 faces, in order to be oriented, towards the external face (3) in an incidence plane P2, forming a angle notably equal to 2θ with the initial incidence plane P1;

after the second crossing of the interface 16-2 and reflection on the external face 3 in an elementary zone 11, and recrossing the interface 2-16, it sustains successively two deflections on the upper face 14 and on the front face 18 and is reoriented in an incidence plane P'1, notably parallel to P1;

after the third crossing of the interface 16-2, the signal then sustains a reflection on the elementary zone 12 of the external face 3 of the plate 1, a crossing of the interface 2-16, and leaves the unit 9 via the output face 17 before being deviated via the optical deflection R2 and the lens L2 towards the receiving cell 5.

The deviation means allow the orientation of the signal S in such a way as to easily place the emitting and receiving means on a same support with the assistance of known means.

There is also a heating element 8 placed on the upper face 14 of the optical unit in order to eliminate condensation that can be formed. From the compactness of the optical unit, the condensation disappeared rapidly and the duration of the heating is greatly reduced.

In another example of production illustrated in FIG. 2a, the input 6' and output 17' faces are placed on the front face 18' of the optical unit 9'. The input 6' and output 17' faces are outlined in the front face 18' and are outlined by a pentagon.

The other elements correspond to those described in reference to FIG. 1a: the emitting means 4, the detection means 5, the optical coupling 7, the rear 15', bottom 16', upper 14', and lateral F1 and F2 faces, the optical deviation means L1 and L2, and the heating element 8'.

The signal S follows an optical trajectory initially oriented to produce an even number of reflections on the external face of the plate 1, four reflections 10', 11', 12', and 13 in the production example, with six deflections in the optical unit 9' between the emitting diode 4 and the photoreceptor cell 5, on the rear 15', upper 14', and front 18' faces.

As is visible on the top view of FIG. 2b, the initial incidence plane Q1 of the signal S in the optical unit makes an angle θ around 10° with a normal N'N to the front or rear faces, 18' or 15', in order to obtain the wanted number of reflections on the external face of the plate and of deflections in the optical unit, respectively four and six in the production example, between the emitting diode and the receiving cell.

The route of the optical signal S thus follows the round trip twice between the front 18' and rear 15' faces of the unit 9', by creating at each time a reflection on the external face of the plate, and the total reflections on the rear, upper, and front faces, by following the parallel directions to the planes Q1 and Q2, the plane Q2 being that of the direction of the output.

The signal S is finally received by the photoreceptor cell 5 according to a direction of receiving D2 of the plane Q2 forming with the plate 1 an angle notably equal to that of the incidence direction.

In order to obtain a more compact unit, the distance between the lateral faces F1 and F2 can be reduced, as illustrated on FIG. 3, by reducing the front face 18" of the unit 9" to the minimum, with a common edge A of the input 6' and output 17' faces. In these conditions, the path of the signal S sustains two reflections, in 10" and 11", on the plate 1 and two deflections, on the rear face 15" and the upper face 14". The heating element 8" also has a reduced surface.

The invention is not limited to the described and represented production examples. For example, the input and output faces can be formed from several spherical or non-spherical surfaces following the incidence and output angle desired, associated to one or several emitters and receptors. In another example, the lenses are Fresnel lenses, able to be associated to the optical deflections. In other examples, a non-spherical lens and a Fresnel lens can serve as the optical input and/or output means. Spherical revolution lenses can also be used.

In order to eliminate all light interference, the faces of the optical unit, other than the total reflection and bottom interface, are covered in a material that absorbs the light signal. In addition, in order to perfect the optical output, the total reflection faces can also be covered by a layer of material reflective to the light signal, or can be covered with a metallic layer, for example, via aluminizing.

In addition, in order to eliminate the light, light interference coming from other light sources can light the unit, for example, sun light, which can disturb the reception of the signal, an interferential filter attached onto the spectral band of the signal is placed between the output face and the receiving means of the signal. To achieve the same goal, it is also possible to mass-color with an attached colorant on the spectral band emitting means.

Moreover, thanks to the optical deviation means, one can place the emitter and receiver, as well as the heat resistant material, on the same support, which notably facilitates their linking to the common electronic treatment circuits necessary for their functioning. These electronic circuits can thus be easily produced on one treatment unit formed on a printed circuit board of reduced dimensions. Such a unit produces a modulation of amplitude for the signal of the emitting diode and a synchronous detection of the signal received by the photo detection cell. Moreover, it is possible to exchange the emitter and the receiver due to the reversible character of the light's route.

In addition, the front and rear deflection faces can be inclined to create a direct deflection of the signal towards the plate without reflection on the upper face.

What is claimed is:

1. A detector of stains for the surface of a transparent plate that has two parallel, opposite faces, an internal face and an external face, the detector, arranged on the internal face of the plate, and including emitting means for emitting a modulated light signal in the direction of the interior of the plate and a receiving means for receiving the signal after the signal has been reflected on the external face of the plate, characterized by also containing an optical unit, made of a material with an index higher than one and transparent to the modulated light signal, the optical unit placed on the internal face of the plate and including at least two deflection faces for the light signal in order to form a trajectory included between the emitting means and the receiving means, and a bottom interface with the internal face of the plate across from a optical coupling means and by deviation means from the signal of the emitting means, so that the signal reflects a first time on the external face of the plate according to a direction included in an initial incidence plane and the deviation means of the signal towards the receiving means, the deflection faces successively orienting the signal towards the external face in at least one incidence plane non-parallel to the initial incidence plane so that the trajectory of the light signal between the emitting means and the receiving means creates at least two reflections on the external face of the plate across from the optical coupling means without reflection on the internal face of the plate.

2. The stain detector according to one of claims 1, characterized by the deflection faces being made up of the rear face, the upper face, and the front face.

3. The stain detector according to claims 1 characterized by the deflection faces being made up of the front face and the rear face, the front face and the rear face being inclined in order to make a direct deflection of the signal towards the plate.

4. The stain detector according to claim 1, characterized by the optical coupling means is formed of silicon.

5. The stain detector according to claim 1, characterized by an interferential filter disposed between the output face and the receiving means attached to the spectral band of the signal to eliminate light interference.

6. The stain detector according to claim 1, characterized by the optical unit and the optical coupling means being mass-colored to eliminate light interference.

7. The stain detector according to claim 1, characterized by a heating element being placed near or against one of the faces of the optical unit in order to eliminate condensation.

8. The stain detector according to claim 1, characterized by the emitting means and the receiving means being attached to a treatment unit formed on a printed circuit board in order to produce a modulation in amplitude of the signal of an emitting diode and a synchronous detection of the signal received by a photo detector cell.

9. The stain detector according to claim 1, characterized by the deflection faces being subjected to a treatment reflecting the light signal.

10. The stain detector according to claim 1, characterized by the faces of the optical unit, other than the deflecting faces and the interface, being covered with a material absorbing the light signal.

11. The stain detector according to claim 1, characterized by the emitting means and the receiving means are placed adjacent to each other.

12. The stain detector according to claim 1, characterized by the deflection faces being subjected to aluminizing.

13. The stain detector according to claim 1, characterized by the deflection faces being covered in a layer of material reflecting the light signal.

14. The stain detector according to claim 1, characterized by the optical unit having a general outline of a parallelepiped rectangle having a front face, an upper face, a rear face, two lateral faces, and a bottom face interfacing with the plate.

15. The stain detector according to claim 14, characterized by the optical coupling means being formed of a flexible layer of material transparent to the light signal, the layer being compressed between bottom face of the optical unit and the internal face of the plate.

16. The stain detector according to claim 14, characterized by the light signal penetrating in the optical unit via an input face situated in the front face of the optical unit, and leaving the optical unit via an output face situated in the front face while the number of reflections on the external face of the plate is even and on the rear face the number of reflections is odd.

17. The stain detector according to claim 16, characterized by the input and output faces of the unit forming lenses.

18. The stain detector according to claim 17, characterized by the lenses being coupled to an optical deflector to define the deviation means.

19. The stain detector according to claim 17, characterized by at least one of the lenses being a convex lens having at least a non-spherical surface.

20. The stain detector according to claim 17, characterized by at least one of the lenses being a convex lens having at least a spherical surface.

21. The stain detector according to claim 17, characterized by at least one of the lenses being a Fresnel lens.

22. The stain detector according to claim 17, characterized by the lenses being an integral part of the optical unit.

* * * * *